(12) United States Patent
Lupotti et al.

(10) Patent No.: US 11,534,538 B2
(45) Date of Patent: Dec. 27, 2022

(54) BLOOD PURIFYING DEVICE INCLUDING PLASMA SEPARATION AND PURIFICATION FILTERS

(71) Applicant: BELLCO S.R.L., Mirandola (IT)

(72) Inventors: Marco Lupotti, Bastiglia (IT); Mary Louise Wratten, Medolla (IT)

(73) Assignee: BELLCO S.R.L., Mirandola (IT)

( * ) Notice: Subject to any disclaimer, the term of this patent is extended or adjusted under 35 U.S.C. 154(b) by 163 days.

(21) Appl. No.: 16/073,641

(22) PCT Filed: Jan. 27, 2017

(86) PCT No.: PCT/EP2017/051817
§ 371 (c)(1),
(2) Date: Jul. 27, 2018

(87) PCT Pub. No.: WO2017/129773
PCT Pub. Date: Aug. 3, 2017

(65) Prior Publication Data
US 2019/0046716 A1 Feb. 14, 2019

(30) Foreign Application Priority Data

Jan. 27, 2016 (IT) .................. 102016000007877

(51) Int. Cl.
*A61M 1/34* (2006.01)
*A61M 1/16* (2006.01)

(52) U.S. Cl.
CPC ........ *A61M 1/3475* (2014.02); *A61M 1/1621* (2014.02); *A61M 1/3486* (2014.02); *A61M 2205/7554* (2013.01)

(58) Field of Classification Search
None
See application file for complete search history.

(56) References Cited

U.S. PATENT DOCUMENTS 6,270,674 B1 * 8/2001 Baurmeister .......... B01D 15/08
210/321.79
2004/0115278 A1 * 6/2004 Putz .................... A61M 1/3486
435/2

(Continued)

FOREIGN PATENT DOCUMENTS

CN   102631722 B   12/2014
FR   2510412 A1    2/1983

OTHER PUBLICATIONS

FR2510412 Messier—Apparatus for blood filtration and purificn [Abstract & MT; Feb. 4, 1983] (Year: 1983).*

(Continued)

*Primary Examiner* — Hayden Brewster
(74) *Attorney, Agent, or Firm* — Shumaker & Sieffert, P.A.

(57) ABSTRACT

A filter for purifying blood (1, 100), comprising a container body (2, 102) in which there are: —an intake port (3, 103) for an incoming blood stream (4, 104), —a first discharge port (5, 105) for an outgoing blood stream (6, 106), and —a second discharge port (7, 107) for a purified plasma stream (8, 108); the container body (2, 102) comprises first filtering means (9, 109) adapted to separate a stream of plasma to be purified (10, 100) from the incoming blood stream (4, 104), and second filtering means (11, 111) adapted to purify the stream of plasma to be purified (10, 110) to obtain the purified plasma stream (8, 108).

20 Claims, 3 Drawing Sheets

(56) References Cited

U.S. PATENT DOCUMENTS

| | | | | |
|---|---|---|---|---|
| 2007/0105156 A1* | 5/2007 | Togawa | ............... | B01D 61/18 |
| | | | | 435/7.1 |
| 2011/0094962 A1 | 4/2011 | Heinrich et al. | | |
| 2012/0058463 A1* | 3/2012 | Deuerlein | ............ | H01F 1/0054 |
| | | | | 435/5 |
| 2015/0273467 A1* | 10/2015 | Sloan | ................ | B01L 3/50273 |
| | | | | 422/513 |
| 2015/0320924 A1* | 11/2015 | Flieg | ................ | B01D 15/3804 |
| | | | | 210/638 |

OTHER PUBLICATIONS

International Preliminary Report on Patentability from International Application No. PCT/EP2017/051817, dated Jul. 31, 2018, 8 pp.
Communication Pursuant to Rules 161(1) and 162 EPC, dated Sep. 13, 2018, from counterpart European Application No. 17701715.9, 3 pp.
Response to Communication pursuant to Rules 161(1) and 162 EPC dated Sep. 13, 2018, from counterpart European Application No. 17701715.9, filed Mar. 6, 2019, 7 pp.
Examination Report from counterpart European Application No. 17701715.9, dated Oct. 7, 2019, 6 pp.
International Search Report for PCT/EP2017/051817 date of completion is Feb. 10, 2017 (two pages).

* cited by examiner

BLOOD PURIFYING DEVICE INCLUDING PLASMA SEPARATION AND PURIFICATION FILTERS

CROSS-REFERENCE TO RELATED APPLICATIONS

This application is a National Stage Application of PCT/EP2017/051817 under 35 USC § 371 (a), which claims benefit of and priority to Italy Patent Application Serial No. 102016000007877 filed Jan. 27, 2016, the disclosures of each of the above-identified applications are hereby incorporated by reference in their entirety.

The present invention relates to a filter for purifying blood, particularly for extracorporeal therapies administered to patients affected by acute organ failure or by acute organ dysfunction, such as acute kidney injury.

In patients affected by organ failure or dysfunction, the organs normally dedicated to eliminating from the bloodstream toxins, inflammation mediators or other unwanted substances present no longer perform this function. As a result of organ failure, the blood progressively retains harmful substances, which, if not eliminated, cause organic damage that can eventually lead to patient death.

Various systems for purifying blood from toxins or other substances such as inflammation mediators and drugs present in blood are used. These systems can act by adsorption of the substances to be eliminated on solid media (perfusion) or by means of ultrafiltration or plasma filtration of the blood through semipermeable membranes. Ultrafiltration can be performed by convection, under the effect of a pressure gradient through the semipermeable membrane (filtration), or by diffusion, contacting one side of the membrane with the blood to be purified and the opposite side with a suitably formulated dialysate solution (dialysis).

Removal of the toxins, of the inflammation mediators, of the drugs or of other poisons from the blood can be performed by blood perfusion or plasma perfusion.

Blood perfusion consists in passing the whole blood through a filter or cartridge that contains an adsorption material, i.e., a resin capable of adsorbing the substances to be removed from the blood.

Plasma perfusion consists in separating plasma from the whole blood and in passing the plasma through a filter or cartridge that contains an adsorption material, i.e., a resin capable of adsorbing the substances to be removed from the blood.

Although blood perfusion has the advantage of being easier to implement, it has several disadvantages, since it can often cause the activation of platelets and cells and the clogging of the resin itself due to protein deposition or coagulation phenomena. Moreover, contact with the whole blood introduces several problems linked to the biocompatibility of the resin itself. In addition, the adsorption capacity of some types of toxins and/or inflammation mediators, particularly cytokines, decreases as the linear velocity with which fluid passes through the resin increases.

The main advantage of plasma perfusion resides in that only the plasma component of whole blood is made to pass through the adsorption filter and since the plasma stream corresponds to approximately 15-30% of the whole blood stream it is possible to maintain lower linear velocities, in practice improving the adsorption yield of the filter, in particular for cytokines and other mediators adsorbed better at low velocities.

However, the main disadvantage of plasma perfusion resides in that the circuits that implement it are more complex and therefore, are often rejected by end-users, who prefer the simpler blood perfusion circuits, despite their inherent limitations.

For purifying blood from toxins, from inflammation mediators, and from unwanted drugs it is known, in extracorporeal therapies, to use disposable circuits, which comprise a filter for separating plasma from whole blood, a filter with adsorption resin for purifying plasma, and a further blood filter. In this manner, it is possible to coordinately use plasma purification along side blood filtration during hemodialysis, or hemodiafiltration, to achieve overall better purification performance.

As an alternative to the use of a plasma separation filter, there is also the possibility to use a filter for blood with high permeability capable of separating the so-called ultrafiltrate instead of the plasma. The ultrafiltrate contains fewer proteins and lipids than in the plasma.

These disposable circuits of the known type also are evidently affected by the drawback of being complex to manufacture, implement and use, due to the plurality of different filters that must be set up and replaced every time.

The aim of the present invention is to provide a blood filter for purifying blood that solves the technical problems described above, obviates the drawbacks and overcomes the limitations of the background art, allowing to make blood purification in extracorporeal therapies easier and simpler.

Within this aim, an object of the present invention is to provide a filter for purifying blood that is easy to provide and economically competitive if compared with the background art.

Another object of the invention is to provide a filter for purifying blood that allows to reduce the quantity of infected disposable material that hospitals have to dispose.

Another object of the invention is to provide a filter for purifying blood that does not have the limitations typical of blood perfusion, yet maintains the advantages of simplicity and straightforwardness.

Another object of the invention is to provide a filter for purifying blood that is efficient in purifying the blood from toxins, inflammation mediators, such as in particular cytokines, drugs, and other types of poison.

Another object of the invention is to provide a filter for purifying blood capable of giving the greatest assurances of reliability and safety in use.

This aim, as well as these and other objects that will become better apparent hereinafter, are achieved by a filter for purifying blood, comprising a container body in which there are:
an intake port for an incoming blood stream,
a first discharge port for an outgoing blood stream, and
a second discharge port for a purified plasma stream,
characterized in that said container body further comprises first filtering means adapted to separate a stream of plasma to be purified from the incoming blood stream, and second filtering means adapted to purify said stream of plasma to be purified to obtain said purified plasma stream.

Further characteristics and advantages of the present invention will become better apparent from the description of two preferred but not exclusive embodiments of a filter for purifying blood, illustrated by way of nonlimiting example with the aid of the accompanying drawings, wherein.

Figure 1:
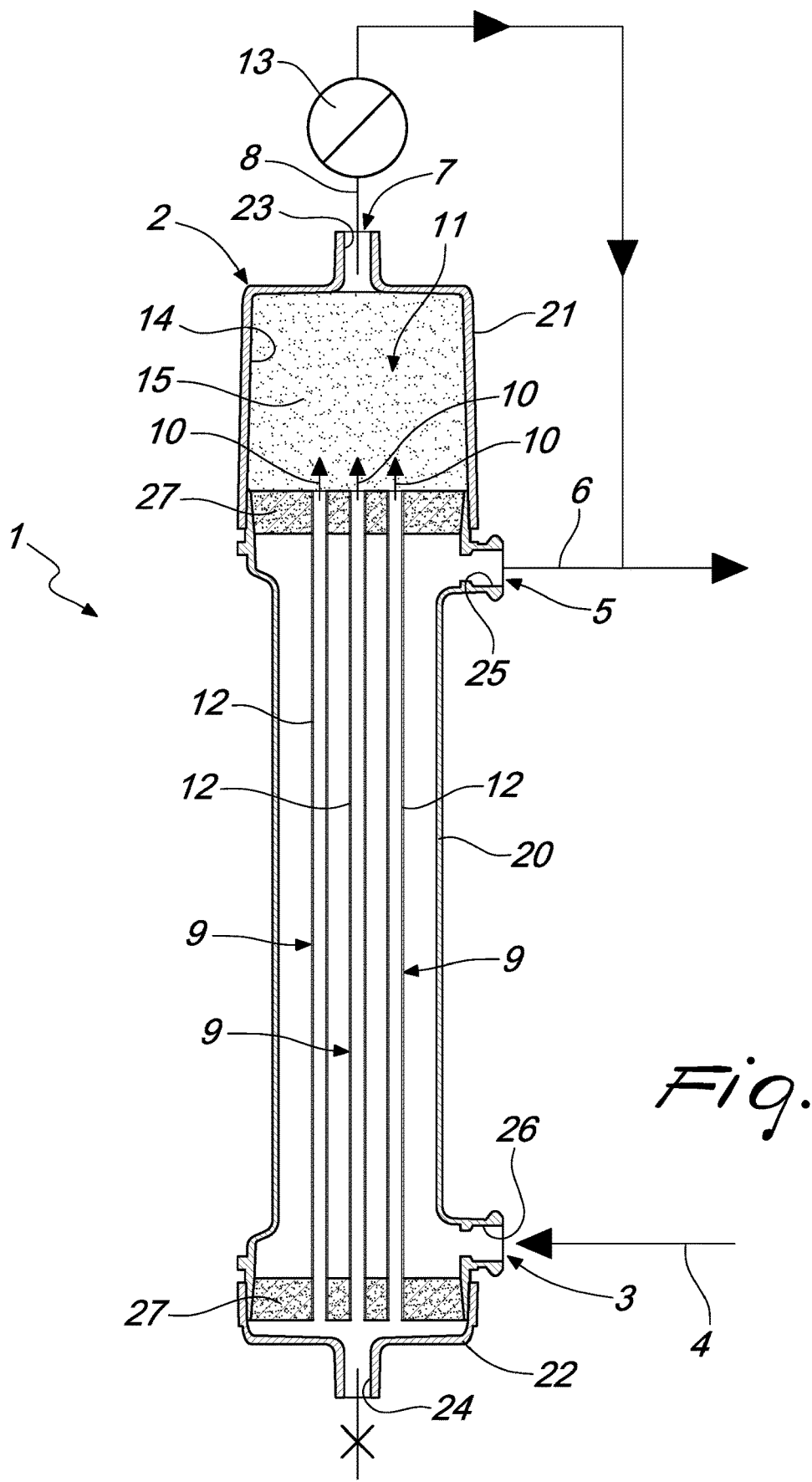
FIG. 1 is a schematic sectional view of a first embodiment of a filter for purifying blood, according to the invention.
Figure 2:
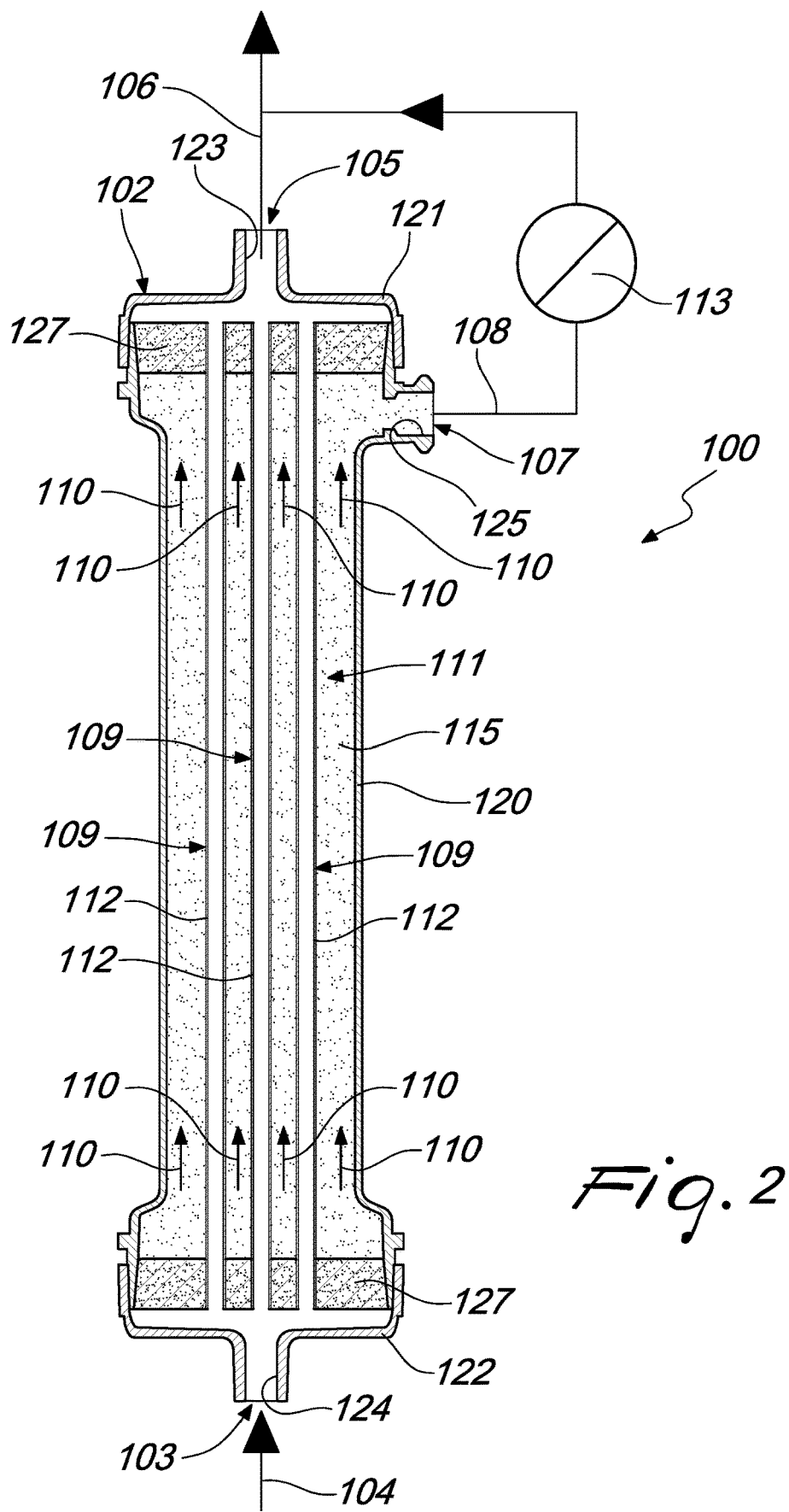
FIG. 2 is a schematic sectional view of a second embodiment of a filter for purifying blood, according to the invention.
Figure 3:
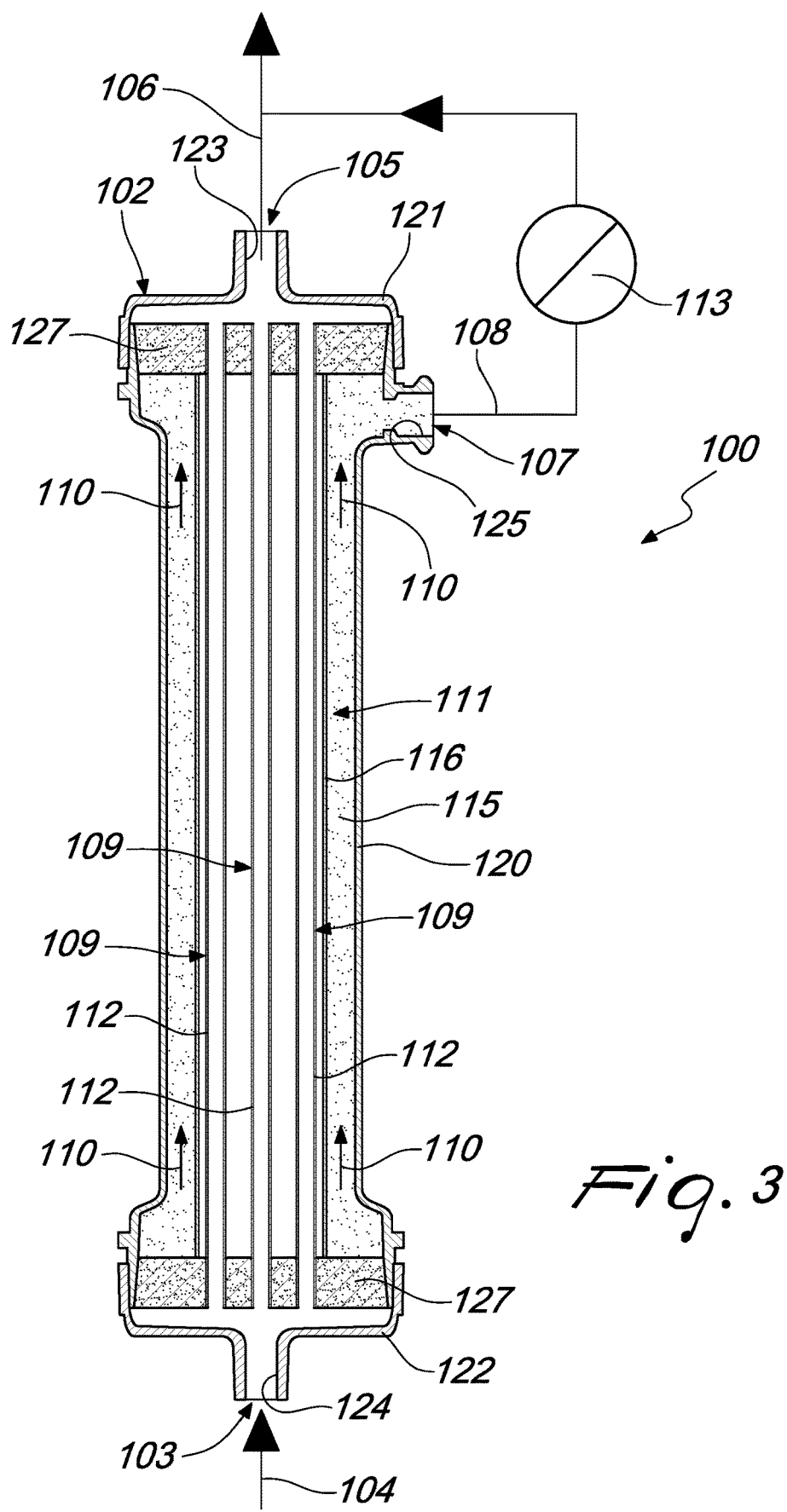
FIG. 3 is a schematic sectional view of a variation of the second embodiment of a filter for purifying blood, according to the invention.

The filter for purifying blood is shown by reference to numeral 1 in the first embodiment in FIG. 1; and by the reference numeral 100 in both the second embodiment in FIG. 2 and the corresponding variation in FIG. 3.

The elements of the second embodiment (FIGS. 2 and 3) that correspond to elements of the first embodiment of FIG. 1 have been designated by the same reference numerals of the first embodiment increased by 100.

The filter 1, 100 comprises a container body 2, 102 in which there are:
- an intake port 3, 103 for an incoming blood stream 4, 104,
- a first discharge port 5, 105 for an outgoing blood stream 6, 106, and
- a second discharge port 7, 107 for a purified plasma stream 8, 108.

According to the invention, the container body 2, 102 comprises first filtering means 9, 109 adapted to separate a stream of plasma to be purified 10, 100 from the incoming blood stream 4, 104, and second filtering means 11, 111 adapted to purify the stream of plasma to be purified 10, 110 to obtain the purified plasma stream 8, 108.

Substantially, the first filtering means 9, 109, which separate the plasma, and the second filtering means 11, 111, which purify the plasma, preferably by adsorption, are both in a same container body 2, 102.

The second filtering means 11, 111 advantageously comprise an adsorbing means 15, 115 configured to retain toxins, inflammation mediators, drugs or poisons of another type present in the stream of plasma to be purified 10, 110.

Preferably, the adsorbing means 15, 115 comprises an adsorption resin. As an alternative, said adsorbing means 15, 115 can be constituted by an adsorption resin.

Advantageously, the second filtering means 11, 111 are adapted to retain cytokines and/or inflammation mediators of the TNF-alpha type, IL-8 and C3adesArg type.

The adsorption resin is advantageously adapted to adsorb proteins with a high affinity with the resin itself. The hydrophobic areas of the adsorption resin can bond to the hydrophobic sites present in cytokines, in toxins, in drugs or in poisons present in the stream of plasma to be purified 10, 110, so that only the most hydrophilic components that belong to the aqueous phase of the plasma may pass through the resin.

Advantageously, the adsorbing means 15, 115 can provide adsorption by other chemical/physical mechanisms, such as bond affinity and/or ion exchange.

Advantageously, the first filtering means 9, 109 comprise a plurality of semipermeable capillary structures 12, 112 and a pump 13, 113 configured to generate a pressure gradient by means of the semipermeable capillary structures 12, 112.

The pressure gradient generated by the pump 13, 113 is advantageously adapted to separate plasma from the incoming blood stream 4, 104, with the semipermeable membranes of the capillary structures 12, 112. The separated stream of plasma 10, 110 is then purified to obtain the purified plasma stream 8, 108.

The container body 2, 102 can comprise a hollow central body 20, 120, which is substantially cylindrical and is closed at its axial ends by a pair of closure caps 21, 121 and 22, 122 also termed ports.

Each one of the closure caps 21, 121, 22, 122 can comprise a hole 23, 123 and 24, 124 connected to the inside of the hollow central body 20, 120. Advantageously, the hole 23, 123 and 24, 124 is extended along the axis of axial extension of the container body 2, 102.

In the present specification the term "port" generally identifies the structure forming a passageway of fluid and the term "hole" is used to identify in the drawings the opening that carries out the function of the corresponding port indicated by an arrow pointing at that opening.

Advantageously, the hollow central body 20, 120 also can comprise, preferably at at least one axial end thereof, a hole 25, 125 that is connected to the inside of the hollow central body 20, 120.

Advantageously, the hole 25, 125 is extended at right angles to the axis of longitudinal extension of the container body 2, 102, i.e., radially with respect to the cylindrical walls of the hollow central body 20, 120.

Advantageously, the container body 2, 102 and in particular the hollow central body 20, 120 and the closure caps 21, 121, 22, 122 can be made of a material such as polycarbonate or polyester.

Advantageously, the semipermeable capillary structures 12, 112 are extended along the axial extension of the container body 20, 120 and are kept in position by a pair of embedding and fixing heads 27, 127 preferably made of a material such as polyurethane.

With particular reference to the first embodiment of the filter for purifying blood 1, shown in FIG. 1, the stream of blood flows advantageously inside the container body 2 outside the semipermeable capillary structures 12, where the stream of plasma to be purified 10 instead flows inside the semipermeable capillary structures 12, drawn inside them by means of a transmembrane pressure gradient.

Advantageously, in the container body 2 there is, in series to the semipermeable capillary structures 12, a chamber 14 that contains the second filtering means 11.

The container body 2 can comprise a hollow central body 20 and at least one closure cap 21 which can be associated with the hollow central body 20, wherein the chamber 14, which contains the second filtering means 11, is provided within the closure cap 21.

As shown in FIG. 1, the hollow central body 20 can comprise, at opposite axial ends thereof, the hole 25 and a second hole 26. Both holes 25 and 26 are connected to the inside of the hollow central body 20 and also are arranged at right angles to the direction of axial extension of container body 2.

In the first embodiment of the filter shown in FIG. 1, the intake port 3 for the incoming blood stream 4 is constituted by the hole 26, while the first discharge port 5 for the outgoing blood stream 6 is constituted by the hole 25.

The blood flows between the two ports 3 and 5 in the volume formed inside the hollow central body 20 all around the semipermeable capillary structures 12. The semipermeable capillary structures separate the stream of plasma 10 to be purified due to the transmembrane pressure gradient imposed by the pump 13. The stream of plasma to be purified 10 therefore penetrates and flows within the semipermeable capillary structures 12 until it reaches the chamber 14, where the adsorption resin of the adsorbent means 15 which purifies the plasma is present. The plasma stream, purified with its passage through the resin of the adsorbing means 15, exits from the second discharge port 7, constituted by the hole 23 provided in the closure cap 21, to be appropriately returned into the outgoing blood stream 6.

Advantageously, the hole 24 provided in the closure cap 22, which is closed during normal use of the filter 1, can be used in a preliminary step of activation of the filter 1, i.e., during so-called priming. In this preliminary step, a physiological or saline solution is introduced in the filter 1 through the hole 24.

With particular reference to the second embodiment of the filter for purifying blood 100, shown in FIGS. 2 and 3, the container body 102 comprises a hollow central body 120 in which the second filtering means 111 are advantageously contained.

Advantageously, as shown in particular in FIG. 2, the adsorbing means 115 comprises a matrix of adsorption resin, contained in the container body 102, in which the semipermeable capillary structures 112 of the filter 100 are embedded.

Advantageously, the stream of blood flows within the container body 102 inside the semipermeable capillary structures 112, while the stream of plasma to be purified 110 flows outside the semipermeable capillary structures 112 through the second filtering means 111.

In the second embodiment of the filter 100, shown in FIG. 2, the intake port 103, for the incoming blood stream 104, to be purified, is constituted by the hole 124 provided in the closure cap 122, while the first discharge port 105 for the outgoing blood stream 106 is constituted by the hole 123 provided in the other closure cap 121.

The blood flows between the two ports 103 and 105 inside the semipermeable capillary structures 112 present in the hollow central body 120. These semipermeable capillary structures 112 separate the stream of plasma to be purified 110 due to the transmembrane pressure gradient imposed by the pump 113. The stream of plasma to be purified 110 exits from the walls of the capillary structures 112 and therefore flows outside the structures 112 directly through the adsorbing means 115 until it reaches the second discharge port 107, constituted by the hole 125. The stream of plasma, purified by the passage through the resin of the adsorbent means 115, can exit from the second discharge port 107, constituted by the hole 125 provided at one end of the hollow central body 120, to be returned appropriately into the outgoing blood stream 106.

With reference instead to the variation of the filter 100, shown in FIG. 3, the first filtering means 109 are separated from the second filtering means 111 with a separation membrane 116. This separation membrane 116 can be advantageously made of a material such as fabric or mesh of suitable loops.

Differently from what is shown in FIG. 2, in the variation of the filter 100 in FIG. 3 the capillary structures 112 are not embedded directly in a resin matrix but are separated from the resin of the adsorbing means 115 by the separation membrane 116. In this manner the plasma, separated from the blood by means of the semipermeable capillary structures 112 by pressure gradient, does not make direct contact immediately with the resin of the adsorbing means 115 but must first also pass through the separation membrane 116.

Therefore, the stream of plasma 110 undergoes purification, by passage through the adsorption resin, in the volume defined by the annular portion that is external to the separation membrane 116.

The operation of the filter for purifying blood 1, 100, in both embodiments described, is clear and evident from what has been described.

In practice it has been found that the filter for purifying blood, according to the present invention, achieves the intended aim and objects, since it allows to perform, within a single container body, both plasma separation and plasma purification.

Another advantage of the filter according to the invention resides because it provides a single device that achieves simultaneously the function of a filter for plasma or of a high-permeability blood filter and of an adsorption filter.

A further advantage of the filter according to the invention resides because it allows a simplification and improvement of the process for the production of filters for purifying blood, since the filter according to the invention can be manufactured in a single process that combines the typical steps of the production of a plasma filter and of an adsorption filter.

A further advantage resides because it makes it easier to implement and use disposable filtering circuits for extracorporeal therapies and reduces the quantity of infected waste material that hospitals must dispose.

Another advantage of the filter according to the invention resides in that it overcomes the criticalities of blood perfusion systems, i.e., the high clogging of the resin, the high activation response of blood platelets and cells, and the need to operate at low linear velocities of the stream of blood, with consequent improvement of adsorption, while maintaining the advantages thereof in terms of simplicity and straightforwardness of use.

A further advantage of the filter according to the invention resides in that it reduces the so-called channeling effect, i.e., the effect that occurs when a preferential flow is established through the central region of a cylindrical filter, therefore clogging the central region of a resin matrix and leaving instead the resin in the peripheral areas without contacting the plasma or the ultrafiltrate.

The filter for purifying blood conceived is susceptible of numerous modifications and variations, all of which are within the abilities of one skilled in the art.

All the details may further be replaced with other technically equivalent elements. In particular, the filter for purifying blood, according to the invention, is also used both to separation and purification of plasma and to separation and purification of an ultrafiltrate.

The materials used, so long as they are compatible with the specific use, and the contingent shapes and dimensions, may be any according to requirements.

The disclosures in Italian Patent Application No. 102016000007877 (UB2016A000013) from which this application claims priority are incorporated by reference.

Where technical features mentioned in any claim are followed by reference signs, those reference signs have been included to increase the intelligibility of the claims and accordingly such reference signs have no limiting effect on the interpretation of each element identified for example by such reference signs.

The invention claimed is:

1. A device comprising:
a container body defining:
an intake port configured to receive an incoming blood stream;
a first discharge port; and
a second discharge port;
a first filter in the container body, the first filter being configured to separate the incoming blood stream into a stream of plasma and an outgoing blood stream, wherein the first filter comprises a plurality of capillary structures configured to separate plasma from the incoming blood stream, and wherein the container body defines a first fluid pathway through which the outgoing blood stream flows to exit the container through the first discharge port; and a second filter in the container body, the second filter being configured to purify the stream of plasma, wherein the container body defines a second fluid pathway through which the stream of plasma flows from the second filter to the second discharge port, and wherein the second filter comprises an adsorbing material, the plurality of capillary structures being embedded in the adsorbing material, wherein the adsorbing material comprises a plurality of hydrophobic areas configured to bond to hydrophobic sites present in any cytokines, toxins, drugs, and poison present in the stream of plasma so that hydrophilic components that belong to an aqueous phase of plasma passes through the adsorbing material, wherein the first filter is configured such that the stream of plasma flows outside the capillary structures of the plurality of capillary structures to the adsorbing material of the second filter and the outgoing blood stream flows inside the capillary structures of the plurality of capillary structures to the first discharge port.

2. The device according to claim 1, wherein the adsorbing material is configured to retain toxins, inflammation mediators, drugs, or poisons of another type that are present in the stream of plasma.

3. The device according to claim 1, wherein the adsorbing material comprises an adsorption resin.

4. The device according to claim 1, wherein the plurality of capillary structures comprises a plurality of semipermeable capillary structures, the device further comprising a pump configured to generate a pressure gradient by means of the semipermeable capillary structures.

5. The device according to claim 1, further comprising a membrane separating the first filter and the second filter.

6. The device according to claim 1, wherein the first filter is configured to draw the plasma from the incoming blood flow into the adsorbing material by a transmembrane pressure gradient.

7. A device comprising:
a container body defining an intake port configured to receive a blood stream;
a first filter in the container body, the first filter comprising a plurality of semipermeable capillary structures configured to separate plasma from the blood stream, the plurality of capillary structures extending from a first end to a second end;
a second filter in the container body, the second filter being configured to purify the plasma separated from the blood stream by the first filter, wherein the second filter comprises an adsorbing material extending along a section of the container body, and wherein the plurality of semipermeable capillary structures extend along at least the section of the container body and extend through the adsorbing material such that the first and second ends of the plurality of semipermeable capillary structures are on opposite sides of the adsorbing material, and
wherein the semipermeable capillary structures of the plurality of semipermeable capillary structures define walls through which the plasma separated from the blood stream flows to the second filter along the section of the container body; and
a membrane separating the first filter and the second filter.

8. The device of claim 7, further comprising a pump configured to generate a pressure gradient that enables the plurality of semipermeable capillary structures to separate the plasma from the blood stream.

9. The device of claim 7, wherein the plurality of semipermeable capillary structures are embedded in the adsorbing material.

10. The device of claim 1, wherein the plurality of capillary structures extend along at least a same length of the container body as the adsorbing material.

11. The device of claim 1, wherein the plurality of capillary structures are embedded in the adsorbing material such that the stream of plasma exits the plurality of capillary structures through walls of the capillary structures and into the adsorbing material.

12. The device of claim 11, wherein the plurality of capillary structures are embedded in the adsorbing material such that the stream of plasma exits the plurality of capillary structures through walls of the capillary structures and directly into the adsorbing material.

13. The device of claim 11, further comprising a membrane between the plurality of capillary structures and the adsorbing material.

14. The device of claim 11, wherein the plurality of capillary structures terminate at first and second ends, and wherein the plurality of semipermeable capillary structures extend through the adsorbing material such that the first and second ends are on opposite sides of the adsorbing material.

15. The device of claim 1, further comprising:
a first fixing head; and
a second fixing head positioned on an opposite side of the absorbing material from the first fixing head, wherein the first and second fixing heads are configured to keep the plurality of capillary structures in position within the container body.

16. The device of claim 7, further comprising:
a first fixing head; and
a second fixing head positioned on an opposite side of the absorbing material from the first fixing head, wherein the first and second fixing heads are configured to keep the plurality of capillary structures in position within the container body.

17. The device of claim 7, wherein the adsorbing material comprises a plurality of hydrophobic areas.

18. The device of claim 17, wherein the plurality of hydrophobic areas are configured to bond to hydrophobic sites of at least one of cytokines, toxins, drugs, or poison present in the plasma so that only hydrophilic components that belong to an aqueous phase of plasma passes through the adsorbing material.

19. The device of claim 7, wherein the membrane comprises a fabric or a mesh.

20. The device of claim 5, wherein the membrane comprises a fabric or a mesh.

* * * * *